US007045652B2

(12) United States Patent
Caron et al.

(10) Patent No.: US 7,045,652 B2
(45) Date of Patent: May 16, 2006

(54) PROCESSES FOR PREPARING SUBSTITUTED ARYL BORONIC ACIDS

(75) Inventors: Stephane Caron, Groton, CT (US); Jolanta Nowakowski, Old Saybrook, CT (US)

(73) Assignee: Pfizer INC, New York, NY (US)

( * ) Notice: Subject to any disclaimer, the term of this patent is extended or adjusted under 35 U.S.C. 154(b) by 27 days.

(21) Appl. No.: 10/453,433

(22) Filed: Jun. 3, 2003

(65) Prior Publication Data

US 2004/0038940 A1 Feb. 26, 2004

Related U.S. Application Data

(60) Provisional application No. 60/393,501, filed on Jul. 3, 2002.

(51) Int. Cl.
C07F 5/02 (2006.01)

(52) U.S. Cl. .............................................. 562/7; 564/8
(58) Field of Classification Search .................... 562/7; 564/8
See application file for complete search history.

(56) References Cited

U.S. PATENT DOCUMENTS

| 5,550,134 A | 8/1996 | Audia et al. |
| 6,235,771 B1 | 5/2001 | Shiraishi et al. |

FOREIGN PATENT DOCUMENTS

| GB | 1064252 | | 4/1967 |
| GB | 1177548 | | 1/1970 |
| GB | 2265373 | * | 9/1993 |
| WO | WO 9834919 | | 8/1998 |

OTHER PUBLICATIONS

Gray et al., 1989, CAS:111:105937.*
Booth et al., 2001, CAS: 136:29259.*
Lindner et al., 1998, CAS:129:122268.*
Sage et al., 1997, CAS: 127:183417.*
Lesuisse et al., 1997, CAS: 127:205360.*
Chan et al., 1994, CAS: 121:96267.*
Spinelli et al., 1966, see CAS: 64:54642.*
Iddles et al., 1940, CAS: 34:10478.*
Fischmeister, 1962, CAS: 56:29335.*
Schaefer et al., 1975, CAS: 82: 105030.*
Simpson et al. 1965, CAS:63:54077.*
Oda et al. 2003, CAS: 138:89831.*
Payne et al., 1975, CAS: 82:97887.*
Artal M C et al; "Synthesis and mesogenic properties of novel board-like liquid crystals" Journal of Materials Chemistry, vol. 11, No. 11, (Oct. 24, 2001), pp. 2801-7, XP009019910 ISSN: 0959-9428 Scheme 1, starting compound Compounds 1c, 2c.

Chaumeil H et al; "Suzuki Cross-Coupling Reaction of Sterically Hindered Aryl Boronates with 3-Iodo-4-methoxybenzoic Acid Methylester" TETRAHEDRON vol. 56, No. 49, (Dec. 1, 2000), pp. 9655-9662, XP004220815 ISSN: 0040-4020 p. 9660, column 1, line 8.

James C A et al; "Combined Directed Metalation—Cross Coupling Strategies, Total Synthesis of the Agloycones of Gilvocarcin V, M and E" TETRAHEDRON Letters, vol. 38, No. 47, (Nov. 24, 1997), pp. 8149-8152, XP004094791 ISSN: 0040-4039 Compound 7a.

Murugesan N et al; "Biphenylsulfonamide endothelin antagonists: structure-activity relationships of a series of mono- and disubstituted analogues and pharmacology of the orally active endothelin antagonist 2'-amino-N-(3, 4-dimethyl-5-isoxazolyl)-4'-(2- methylpropyl)'1,1'-biphenyll-2-sulfonamide (BMS-187308)" Journal of Medicinal Chemistry, vol. 41, No. 26, (Dec. 17, 1998), pp. 5198-5218, XP002201680 ISSN: 0022-2623 Scheme 1a, step (c) & Table 2, Compounds 6s & 6t GB 1 177 548 A (ICI LTD) (Jan. 14, 1970) example 4.

Comber M F et al; "The synthesis of hallachrome leucotriacetate (2,7,8-triacetoxy-1-methoxy-3-methylanthracene)" Australian Journal of Chemistry, vol. 38, No. 10, 1985, pp. 1481-1490, XP009019901 ISSN: 0004-9425 Compound 8.

Miller B et al; "Effects of halogen substitution on reactions of o-quinol acetates with isopropylmagnesium bromide and diisopropylmagnesium. Competition between unimolecular decomposition and bimolecular reactions of radicia anions" Journal of Organic Chemistry, vol. 51, No. 2, (Jan. 24, 1986), pp. 174-179, XP002289864 ISSN: 0022-3263 p. 179, col. 2, line 15-line 18.

(Continued)

Primary Examiner—Taofiq Solola
Assistant Examiner—Robert Shiao
(74) Attorney, Agent, or Firm—Steve Zelson; Israel Nissenbaum

(57) ABSTRACT

The invention relates to processes for preparing a compound of the formula (V)

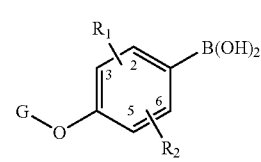

and alkyl boronic esters thereof wherein $R^1$ is attached at the 2 or 3 position of the benzene ring, $R^2$ is attached at the 5 or 6 position, and $R^1$, $R^2$ and G are as defined herein. Said compound is a key synthetic intermediate in the preparation of 2-amino-6-(substituted-4-phenoxy)-substituted-pyridines useful as nitric oxide synthase (NOS) inhibitors in a mammal.

3 Claims, No Drawings

OTHER PUBLICATIONS

Gilman H et al; "Some substituted alpha-(aryloxy)-isobutyric acids" Journal of the American Chemical Society, vol. 77, No. 24, (Dec. 25, 1955), pp. 6644-6646, XP002259865 ISSN: 0002-7863 table 1.

Leznoff C C et al; "Octaarylethynyl and octaarylbutadiynyl phthalocyanimes" Canadian Journal of Chemistry, vol. 79, No. 5-6, (May 2001), pp. 878-887, XP009019902 ISSN: 0008-4042 Compound 5.

Bruce D W et al; "Electronice hyperpolarisabilities of some mesogenic stilbazole compleses of Rh(l) and Ir(l)" Molecular Crystals and Liquid Crystals, vol. 231, 1993, pp. 253-256, XP009019903 ISSN: 1058-725X p. 225, line 1.

Diana G D et al; "Antiviral activity of some beta-diketones, 2, Aryloxy alkyl diketones, In vitro activity against both RNA and DNA viruses" Journal of Medicinal Chemistry, vol. 20, No. 6, 1977, pp. 757-761, XP002259866 ISSN: 0022-2623 Compound III precursor of compounds 9 & 14 in Table 1.

Freudenmann R et al; "Synthesis of conjugated-bridged triphenylenes and application in OLEDs" Journal of Materials Chemistry, vol. 11, No. 6, (May 24, 2001), pp. 1618-1624, XP009019895 ISSN: 0959-9428 Compounds 3b & 3c.

Hall A W et al; "Synthesis and evaluation of a series of novel 2-substituted poly (allyl alcohol) side chain liquid crystalline oligomers exhibiting ferroelectricity" Liquid Crystals, vol. 20, No. 4, (Apr. 1, 1996), pp. 437-447, XP000589680 ISSN: 0267-8292 p. 438—compounds 1,2, & 3 & step (ii).

Gilman H et al; "Hydroxybenzeneboronic acids and anhydrides" Journal of the American Chemical Society, vol. 79, No. 12, (Jun. 20, 1957), pp. 8077-8081, XP002259867 ISSN: 0002-7863 Paragraph bridging columns on page 3080.

Matsubara H et al; "Synthesis and properties of ferroelectric liquid crystalline compounds incorporating a 1,3,2-dioxaborinane ring" Molecular Crystals and Liquid Crystals, vol. 180B, 1990, pp. 337-342, XP009020189 ISSN: 0026-8941 Scheme 1 & Table 1.

* cited by examiner

PROCESSES FOR PREPARING SUBSTITUTED ARYL BORONIC ACIDS

This application claims priority under 35 USC 119 of U.S. Provisional 60/393,501, filed Jul. 3, 2002.

BACKGROUND OF THE INVENTION

This invention relates to a new route for the preparation of substituted-aryl boronic acid derivatives which are useful intermediates in the preparation of 2-amino-6-(2-substituted-4-phenoxy)-substituted-pyridines that exhibit activity as nitric oxide synthase (NOS) inhibitors. Examples of 2-amino-6-(2-substituted-4-phenoxy)-substituted-pyridines that are prepared from substituted-aryl boronic acid derivatives are disclosed in PCT international application publication number WO 98/34919, published Aug. 13, 1998, and incorporated herein by reference in its entirety.

The 2-amino-6-(2-substituted-4-phenoxy)-substituted-pyridines disclosed in WO 98/34919 as nitric oxide synthase (NOS) inhibitors are useful in the treatment of migraine inflammatory diseases, stroke, acute and chronic pain, hypovolemic shock, traumatic shock, reperfusion injury, Crohn's disease, ulcerative colitis, septic shock, multiple sclerosis, AIDS associated dementia, neurodegenerative diseases, neuron toxicity, Alzheimer's disease, chemical dependencies and addictions, emesis, epilepsy, anxiety, psychosis, head trauma, adult respiratory distress syndrome (ARDS), morphine induced tolerance and withdrawal symptoms; inflammatory bowel disease, osteoarthritis, rheumatoid arthritis, ovulation, dilated cardiomyopathy, acute spinal cord injury, Huntington's disease, Parkinson's disease, glaucoma, macular degeneration, diabetic neuropathy, diabetic nephsopathy and cancer in a mammal.

SUMMARY OF THE INVENTION

The present invention relates to a process of preparing a compound of the formula

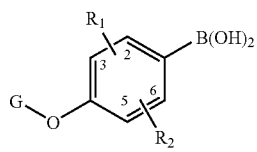

V said compound of formula V useful as a synthetic intermediate in the preparation of a 2-amino-6-(substituted-4-phenoxy)-substituted-pyridine of the formula

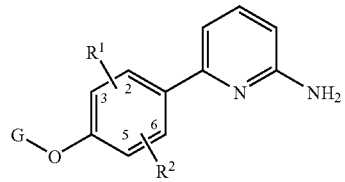

VI wherein in said compound of formula V $R^1$ is attached at carbon 2 or carbon 3 and $R^2$ is attached at carbon 5 or carbon 6 of the aryl moiety;

each $R^1$ and $R^2$ is independently selected from the group consisting of H, $(C_1-C_6)$alkyl, $(C_2-C_6)$alkenyl, $(C_1-C_6)$alkoxy-$(C_1-C_3)$alkyl, halo, $(C_1-C_6)$alkoxy, $(C_1-C_7)$alkyl, $(C_2-C_{10})$alkoxyalkyl, and a $—CH_2(CH_2)_{1-4}CH_2—$ group having a first carbon and a terminal carbon with the proviso that said first carbon is attached to carbon 2 of the aryl moiety and said terminal carbon is attached to carbon 3 of the aryl moiety so that a ring connects carbon 2 and carbon 3 of the aryl moiety or said first carbon is attached to carbon 5 of the aryl moiety and said terminal carbon is attached to carbon 6 of the aryl moiety so that a ring connects carbon 5 and carbon 6 of the aryl moiety;

G is hydrogen, aminocarbonyl-$(C_1-C_3)$alkyl-, aminocarbonyl-$(C_1-C_3)$alkyl, di-$[(C_1-C_3)$alkyl]-$(C_1-C_3)$alkyl-, and $N(R^3)(R^4)(C_1-C_4)$alkyl, wherein $R^3$ and $R^4$ are selected, independently, from hydrogen, $(C_1-C_7)$alkyl, tetrahydronaphthalene and arylalkyl, wherein the aryl moiety of said arylalkyl is phenyl or naphthyl and the alkyl moiety is straight or branched and contains from 1 to 6 carbon atoms, and wherein said $(C_1-C_7)$alkyl and said tetrahydronaphthalene and the aryl moiety of said arylalkyl may optionally be substituted with from one to three substituents, preferably from zero to two substituents, that are selected, independently, from fluoro, chloro, $(C_1-C_4)$alkoxy, and $(C_1-C_4)$alkylamino;

or $R^3$ and $R^4$ form, together with the nitrogen to which they are attached, a piperazine, piperidine, azetidine or pyrrolidine ring or a saturated or unsaturated azabicyclic ring system containing from 6 to 14 ring members, from 1 to 3 of which are nitrogen, from zero to two of which are oxygen, and the rest of which are carbon;

and wherein said piperazine, piperidine, azetidine and pyrrolidine rings and said azabicyclic ring systems may optionally be substituted with one or more substituents, preferably with from zero to two substituents, that are selected, independently, from $(C_1-C_6)$alkyl, amino, $(C_1-C_6)$alkylamino, [di-$(C_1-C_6)$alkyl]amino, phenyl substituted 5 to 6 membered heterocyclic rings containing from 1 to 4 ring nitrogen atoms, and wherein the phenyl moieties of any of the foregoing substituents may optionally be substituted with one or more substituents, preferably with from zero to two substituents, that are selected, independently, from fluoro, chloro, $(C_1-C_3)$alkyl, $(C_1-C_3)$alkoxy, $CF_3$ and $OCF_3$;

and wherein said piperazine, piperidine, azetidine and pyrrolidine rings and said azabicyclic ring systems may be attached to $—(C_0-C_4)$alkyl-O— (wherein the oxygen of said $—C_0-C_4$)alkyl-O— is the oxygen atom depicted in structural formula V) at a nitrogen atom of the $NR^3R^4$ ring or any other atom of the ring having an available bonding site;

or G is a group of the formula A

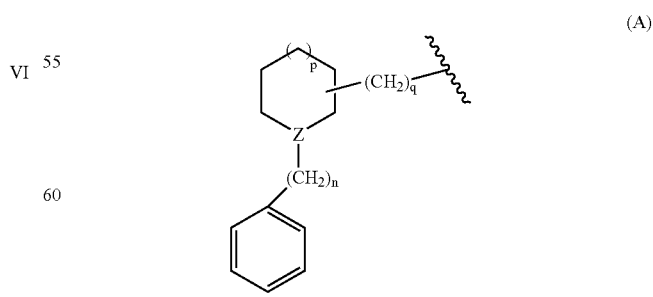

(A)

wherein Z is nitrogen or CH, n is zero or one, q is zero, one, two or three and p is zero, one or two;

which comprises treating a compound of the formula IV

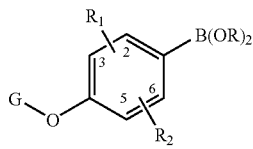

wherein R is $(C_1-C_6)$alkyl and $R^1$, $R^2$, G, $R^3$ and $R^4$ are as defined above with a base and then acidifying to form said boronic acid of formula V.

In a further embodiment of the process said G moiety of formula IV, V or VI is $NR^3R^4(C_1-C_4)$alkyl and $NR^3R^4$ is a piperidine, piperazine, azetidine or pyrrolidine ring or a group of the formula

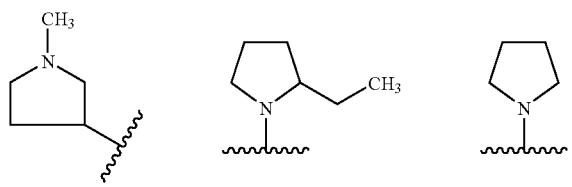

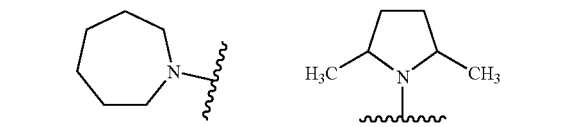

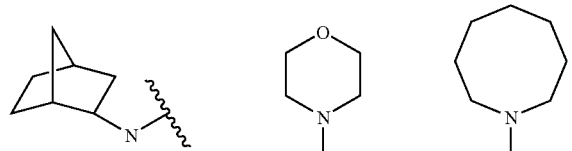

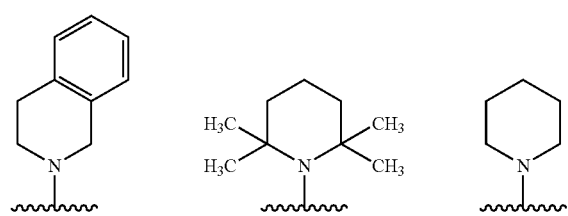

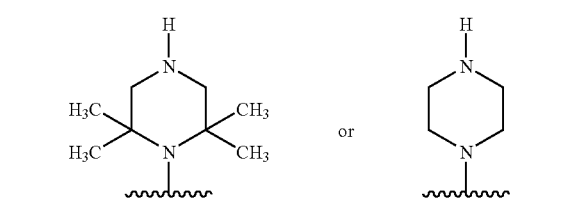

In a still further aspect of the process G is benzyl and the group GO— is replaced with fluoro.

In yet another aspect of the process of the present invention, compound IV, wherein R, $R^1$, $R^2$, G, $R^3$ and $R^4$ are as defined above is prepared by treating a compound of the formula

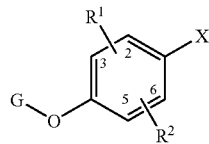

wherein $R^1$, $R^2$, G, $R^3$ and $R^4$ are as defined above and X is selected from bromo or iodo with (1) $C_1-C_{10}$ alkyl lithium and (2) a $C_1-C_6$ trialkyl borate.

In said process of making the compound of formula IV, in a preferred embodiment X is bromo and said compound of formula III is treated with (1) an organolithium agent selected from butyl lithium, t-butyl lithium, pentyl lithium or hexyl lithium, preferably hexyl lithium and (2) said trialkyl borate selected from trimethylborate, triethylborate or tri-isopropylborate, preferably trimethylborate.

In a further aspect of the invention, the compound of formula III wherein $R^1$, $R^2$, G, $R^3$ and $R^4$ are as defined above is prepared by treating a compound of the formula

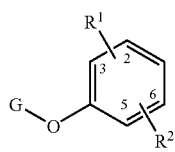

wherein $R^1$, $R^2$, G, $R^3$ and $R^4$ areas defined above with a brominating or iodinating agent, selected from iodine, N-iodosuccinimide, bromine and N-bromosuccinimide, preferably a brominating agent selected from bromine and N-bromosuccinimide, most preferably N-bromosuccinimide.

In yet a further aspect of the invention the compound of formula II, wherein $R^1$, $R^2$, G, $R^3$ and $R^4$ are as defined above, is prepared by treating a compound of the formula

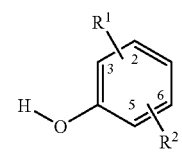

wherein $R^1$ and $R^2$ are as defined above, with an alkylating agent GY wherein G is as defined above and Y is a moiety that is displaced by the phenolic oxygen of compound I said moiety selected from halo, $C_1-C_4$ perfluoroalkylsulfonate, tosylate, methanesulfonate, preferably chloro and bromo under basic conditions using a base selected from sodium hydroxide, potassium hydroxide, sodium carbonate, sodium bicarbonate, potassium carbonate, potassium bicarbonate or cesium carbonate, preferably potassium carbonate and potassium hydroxide.

The term "halo", as used herein, unless otherwise indicated, means fluoro, chloro, bromo or iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived form an aromatic hydrocarbon by removal of one hydrogen or an aromatic carbocyclic ring to which substituents are attached.

DETAILED DESCRIPTION OF THE INVENTION

The process of the present invention and the preparation of the compounds of the present invention are illustrated in the following Scheme. The preparation of the compounds of formulas II–V are described in the Scheme and discussion that follow, wherein, unless otherwise indicated, R, $R^1$, $R^2$, $R^3$, $R^4$, G, X, Y and Z are as defined above.

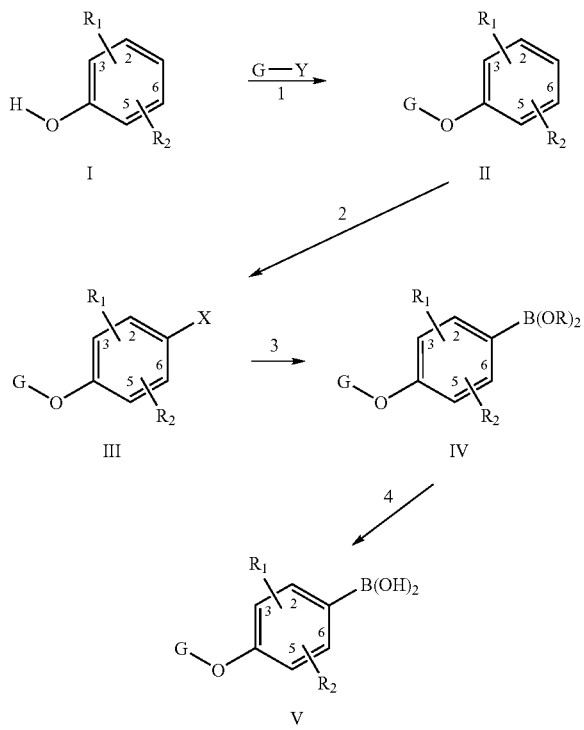

Overall the synthetic sequence of the scheme involves alkylation of the phenolic oxygen of compound I (step 1) to form alkylated phenol having structure II, bromination or iodination, preferably bromination, of alkylated phenol II (step 2) to form halogenated aryl III, treating compound III with an organolithium reagent to replace halogen X, wherein X is bromo or iodo, with lithium and reaction of the intermediate aryllithium with an alkyl borate (step 3) to form compound IV wherein R is $C_1$–$C_6$ alkyl and hydrolysis with base to form a boronic acid salt from which the boronic acid V is obtained by acidification (step 4).

In step 1 of the scheme alkylation of phenol I is carried out in solution in a solvent such as diethylether, tetrahydrofuran, glyme or diglyme, preferably tetrahydrofuran. A solution of phenol I is added to a mixture of an alkylating agent GY, wherein G is as defined above and Y is a moiety or functional group that is displaced by the phenolic oxygen of compound I as defined above, preferably chloro, bromo and iodo and a base such as sodium hydroxide, potassium hydroxide, sodium carbonate, sodium bicarbonate, potassium carbonate, potassium bicarbonate or cesium carbonate, preferably potassium carbonate and potassium hydroxide followed by addition of a second solvent such as heptane, hexane or toluene, preferably toluene. The reaction mixture is stirred at a temperature between about 25° C. and about 100° C., preferably about 75° C. for a period of about 3 to about 48 hours, preferably about 28 hours to afford a compound of formula II.

Step 2 of the scheme is halogenation of aryl II. A solution of compound of formula II in a solvent such as methanol, ethanol, propanol, isopropanol, preferably methanol is protected from light and cooled to a temperature between about –10° C. to about 10° C., preferably about 0° C. followed by addition of either sodium or potassium bromide for bromination or sodium or potassium iodide for iodination, preferably sodium bromide for bromination. A brominating agent such as bromine or N-bromosuccinamide, or an iodinating agent, such as iodine or N-iodosuccinimide, preferably N bromosuccinamide is added and the resultant mixture is stirred at about 0° C. to about 30° C., preferably at about 25° C. for a period of about 30 minutes to about 5 hours, preferably about one hour to afford a compound of formula III.

Step 3 of the scheme is formation of boronic acid ester IV. Aryl bromide III is dissolved in an aprotic solvent preferably an ethereal solvent such as diethylether, tetrahydrofuran, glyme or diglyme, most preferably tetrahydrofuran and cooled to a temperature between about –30° C. to about –100° C., preferably to about –78° C. and is treated with an organolithium reagent such as butyllithium, t-butyllithium, pentyllithium or hexyllithium, preferably hexyllithium for a period between about 15 to about 120 minutes, preferably about 30 minutes to form an organolithium compound wherein lithium is exchanged for the bromine substituent introduced in step 2 of the scheme. The lithium compound thus formed is then reacted with a $C_1$–$C_6$ trialkylborate preferably trimethylborate, triethylborate or triisopropylborate, most preferably trimethylborate with said trialkylborate added over a period of about 0.5 to about 6 hours, preferably about 3 hours while maintaining the temperature between about –30° C. to about –80° C., preferably at about –78° C. to afford arylboronic ester IV wherein R is $C_1$–$C_6$ alkyl.

In step 4 of the scheme arylboronic acid V is obtained by hydrolyzing arylboronic ester IV with cooled excess base, said base selected from sodium hydroxide, potassium hydroxide or cesium hydroxide, preferably sodium or potassium hydroxide, to form a salt of said arylboronic acid V and then adjusting the pH to about 10.5 to about 11.5, preferably about 11.

The present invention is illustrated by the following examples, but it is not limited to the details thereof.

EXAMPLE 1

[2-(2-ethyl-5-methoxy-phenoxy)-ethyl]-dimethylamine

To a solution of 3-ethyl-5-methoxy-phenol (103.8 g, 682 mmol) in tetrahydrofuran (490 mL) was added a mixture of potassium hydroxide (75.8 g, 887 mmol), potassium carbonate (235.7 g, 1.71 mol, powder form), and 1-chloro-2- dimethylamino-ethane hydrochloride (98.2 g, 682 mmol) followed by addition of toluene (1.10 L). The mixture was stirred at 75° C. for 28 hours. The reaction mixture was poured into ice-cold water (1.0 L). The organic layer was washed with water (1.0 L) and then twice with 1L of 1 M HCl. Saturated aqueous solution of sodium bicarbonate (1.2 L) was added to the combined aqueous extracts, the pH was adjusted to 11 with 30% sodium hydroxide solution (220 mL). The product was extracted from the aqueous phase with two 0.8 L portions of tert-butylmethylether. The combined organic extracts were concentrated to give 144.2 g (91% yield) of [2-(2-ethyl-5-methoxy-phenoxy)-ethyl]-dimethyl-amine as a yellow oil.

$^1$H NMR (CDCl$_3$, 400 MHz): δ=1.16 (t, J=7.5 Hz, 3H), 2.36 (s, 6H), 2.57 (q, J=7.5 Hz, 2H), 2.77 (t, J=6.0 Hz, 2H), 3.78 (s, 3H), 4.06 (t, J=6.0 Hz, 2H), 6.41–6.44 (m, 2H), 7.04 (m, 1H).

EXAMPLE 2

[2-(4-bromo-2-ethyl-5-methoxy-phenoxy)-ethyl]-dimethyl-amine

A solution of [2-(2-ethyl-5-methoxy-phenoxy)-ethyl]-dimethyl-amine (143.6 g, 0.64 mol) in methanol (1.3 L) was protected from light. To the solution cooled in an ice-bath was added sodium bromide (66.2 g, 0.64 mol) followed by portionwise addition of N-bromosuccinamide (114.5 g, 0.64 mol) to maintain the temperature at 20° C. The clear yellow solution was stirred at room temperature for 1 hour and then poured into a 10% sodium thiosulfate solution (1.5 L) and finally extracted with one 1L portion and two 0.5L portions of tert-butylmethylether. The combined organic extracts were washed twice with 0.5L of water, and then concentrated to afford 184.09 (94% yield) of [2-(4-bromo-2-ethyl-5-methoxy-phenoxy)-ethyl]-dimethyl-amine as an orange oil.

$^1$H NMR (CDCl$_3$, 400 MHz): δ=1.15 (t, J=7.5 Hz, 3H) 2.36 (s, 6H), 2.55 (dq, J=7.5 Hz, J=0.5 Hz, 2H), 2.76 (t, J=6.0 Hz, 2H), 3.87 (s, 3H), 4.07 (t, J=6.0 Hz, 2H), 6.47 (s, 1H), 7.26 (t, J=0.5 Hz, 1H).

EXAMPLE 3

[4-(2-Dimethylamino-ethoxy)-5-ethyl-2-methoxy]-phenyl-boronic acid

Under an inert atmosphere, [2-(4-bromo-2-ethyl-5-methoxy-phenoxy)-ethyl]-dimethyl-amine (179.8 g, 595 mmol) was dissolved in tetrahydrofuran (0.86 L). The reaction mixture was cooled to −78° C. and then a 2.5 M solution of hexyllithium in hexane (250 mL, 625 mmol) was added over a 3 hour period while maintaining the temperature at or below −75° C. The mixture was stirred for 30 minutes. Trimethylborate (99.5 mL, 892 mmol) was added over a 3 hour period keeping the temperature between −75° C. and −78° C. After 5 minutes the cooling bath was removed and the mixture was allowed to warm to −50° C. (30 minutes) and then poured on cooled 1M sodium hydroxide solution (2.0L). The resultant mixture was extracted with two 0.5 L portions of tert-butylmethylether. A saturated sodium bicarbonate solution (0.5 L) was added to the aqueous layer and the pH was adjusted to 11 with 32% hydrochloric acid (165 mL). The precipitated product was extracted with two 2.0 L portions and one 0.2 L portion of tert-butylmethylether. The organic extracts were combined and concentrated to give 127.3 g (81% yield) of [4-(2-dimethylamino-ethoxy)-5-ethyl-2methoxy]-phenyl-boronic acid as a yellow solid, m.p. 99° C. (decomposition at 102° C.).

$^1$H NMR (CDCl$_3$, 400 MHz): δ=1.16 (t, J=7.5 Hz, 3H), 2.39 (s, 6H), 2.58 (q, J=7.5 Hz, 2H), 2.82 (t, J=5.9 Hz, 2H), 3.89 (s, 3H), 4.15 (t, J=5.9, 2H), 6.27 (bs, 2H) 6.43 (s, 1H), 7.57 (s, 1H).

What is claimed is:

1. A compound of the formula

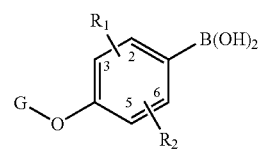

V or a salt thereof, wherein $R^1$ is attached at carbon 2 or 3 and the $R^2$ is attached at carbon 5 or 6 of the aryl moiety;

each $R^1$ and $R^2$ is independently selected from the group consisting of $(C_1-C_6)$alkyl, $(C_2-C_6)$alkenyl, $(C_1-C_6)$alkoxy-$(C_{1-C3})$alkyl, fluoro, chloro, $(C_1-C_6)$alkoxy, $(C_1-C_7)$alkyl, and $(C_2-C_{10})$alkoxyalkyl, and a —CH$_2$(CH$_2$)$_{1-4}$CH$_2$— group having a first carbon and a terminal carbon with the proviso that said first carbon is attached to carbon 2 of the aryl moiety and said terminal carbon is attached to carbon 3 of the aryl moiety so that a ring connects carbon 2 and carbon 3 of the aryl moiety or said first carbon is attached to carbon 5 of the aryl moiety and said terminal carbon is attached to carbon 6 of the aryl moiety so that a ring connects carbon 5 and carbon 6 of the aryl moiety;

G is aminocarbonyl-$(C_1-C_3)$alkyl-, aminocarbonyl-$(C_1-C_3)$alkyl, di-[$(C_1-C_3)$alkyl]-$(C_1-C_3)$alkyl-, and N($R^3$)($R^4$)$(C_1-C_4)$alkyl, wherein $R^3$ and $R^4$ are selected, independently, from hydrogen, $(C_1-C_7)$alkyl, tetrahydronaphthalene and arylalkyl, wherein the aryl moiety of said arylalkyl is phenyl or naphthyl and the alkyl moiety is straight or branched and contains from 1 to 6 carbon atoms, and wherein said $(C_1-C_7)$alkyl and said tetrahydronaphthalene and the aryl moiety of said arylalkyl may optionally be substituted with from one to three substituents, preferably from zero to two substituents, that are selected, independently, from fluoro, chloro, amino, $(C_1-C_4)$alkoxy, and $(C_1-C_4)$alkylamino;

or G is a group of the formula A

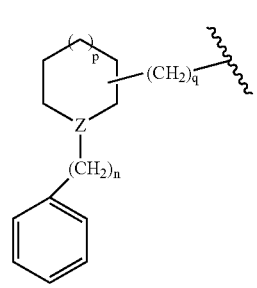

(A)

wherein Z is CH, n is zero or one, q is zero, one, two or three and p is zero, one or two.

2. A compound of the formula

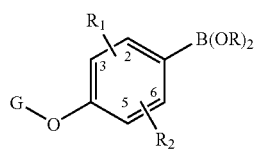

(IV)

wherein R is $(C_1-C_6)$alkyl;

$R^1$ is attached at carbon 2 or 3 and the $R^2$ is attached at carbon 5 or 6 of the aryl moiety;

each $R^1$ and $R^2$ is independently selected from the group consisting of H, $(C_1-C_6)$alkyl, $(C_2-C_6)$alkenyl, $(C_1-C_6)$alkoxy-$(C_1-C3)$alkyl, fluoro, chloro, $(C_1-C_6)$alkoxy, $(C_1-C_7)$alkyl, and $(C_2-C_{10})$alkoxyalkyl, and a —CH$_2$(CH$_2$)$_{1-4}$CH$_2$— group having a first carbon and a terminal carbon with the proviso that said first carbon is attached to carbon 2 of the aryl moiety and said terminal carbon is attached to carbon 3 of the aryl moiety so that a ring connects carbon 2 and carbon 3 of the aryl moiety or said first carbon is attached to carbon 5 of the aryl moiety and said terminal carbon is attached to carbon 6 of the aryl moiety so that a ring connects carbon 5 and carbon 6 of the aryl moiety;

G is hydrogen, aminocarbonyl-$(C_1-C_3)$alkyl-, aminocarbonyl-$(C_1-C_3)$alkyl, di-[$(C_1-C_3)$alkyl]-$(C_1-C_3)$alkyl-, and N($R^3$)($R^4$)$(C_1-C_4)$alkyl, wherein $R^3$ and $R^4$ are selected, independently, from hydrogen, $(C_1-C_7)$alkyl, tetrahydronaphthalene and arylalkyl, wherein the aryl moiety of said arylalkyl is phenyl or naphthyl and the alkyl moiety is straight or branched and contains from 1 to 6 carbon atoms, and wherein said $(C_1-C_7)$alkyl and said tetrahydronaphthalene and the aryl moiety of said arylalkyl may optionally be substituted with from one to three substituents, preferably from zero to two substituents, that are selected, independently, from fluoro, chloro, amino, $(C_1-C_4)$alkoxy, and $(C_1-C_4)$alkylamino;

or G is a group of the formula A

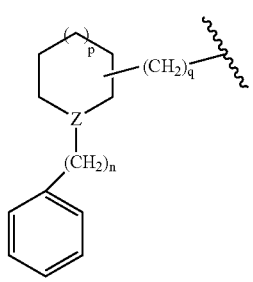

(A)

wherein Z is CH, n is zero or one, q is zero, one, two or three and p is zero, one or two with the proviso that $R^1$ and $R^2$ are not both H.

3. A compound of the formula

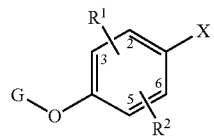

III wherein X is selected from bromo and iodo;

$R^1$ is attached at carbon 2 or 3 and $R^2$ is attached at carbon 5 or 6 of the aryl moiety;

each $R^1$ and $R^2$ is independently selected from the group consisting of $(C_1-C_6)$alkyl, $(C_2-C_6)$alkenyl, $(C_1-C_6)$alkoxy-$(C_1-C_3)$alkyl, fluoro, chloro, $(C_1-C_6)$alkoxy, $(C_1-C_7)$alkyl, and $(C_2-C_{10})$alkoxyalkyl, and a —CH$_2$(CH$_2$)$_{1-4}$CH$_2$— group having a first carbon and a terminal carbon with the proviso that said first carbon is attached to carbon 2 of the aryl moiety and said terminal carbon is attached to carbon 3 of the aryl moiety so that a ring connects carbon 2 and carbon 3 of the aryl moiety or said first carbon is attached to carbon 5 of the aryl moiety and said terminal carbon is attached to carbon 6 of the aryl moiety so that a ring connects carbon 5 and carbon 6 of the aryl moiety;

G is aminocarbonyl-$(C_1-C_3)$alkyl, di-[$(C_1-C_3)$alkyl]-$(C_1-C_3)$alkyl-, and N($R^3$)($R^4$)$(C_1-C_4)$alkyl, wherein $R^3$ and $R^4$ are selected, independently, from hydrogen, $(C_1-C_7)$alkyl, tetrahydronaphthalene and arylalkyl, wherein the aryl moiety of said arylalkyl is phenyl or naphthyl and the alkyl moiety is straight or branched and contains from 1 to 6 carbon atoms, and wherein said $(C_1-C_7)$alkyl and said tetrahydronaphthalene and the aryl moiety of said arylalkyl may optionally be substituted with from one to three substituents, preferably from zero to two substituents, that are selected, independently, from fluoro, chloro, amino, $(C_1-C_4)$alkoxy, and $(C_1-C_4)$alkylamino;

or G is a group of the formula A

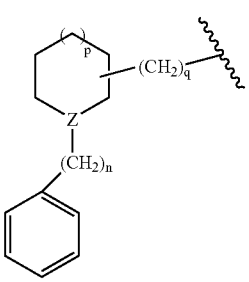

(A)

wherein Z is CH, n is zero or one, q is zero, one, two or three and p is zero, one or two.

* * * * *